US012740988B2

(12) United States Patent
Patil et al.

(10) Patent No.: US 12,740,988 B2
(45) Date of Patent: Sep. 22, 2026

(54) PHARMACEUTICAL COMPOSITION COMPRISING MELOXICAM

(71) Applicant: Mylan Laboratories Limited, Hyderabad (IN)

(72) Inventors: Pankaj Devidas Patil, Hyderabad (IN); Vivekanand Khyamgonde, Hyderabad (IN); Ritesh Kakaria, Hyderabad (IN); Ashish Jaiswal, Hyderabad (IN); Akhilesh Dixit, Hyderabad (IN); Santanu Chakraborty, Hyderabad (IN); Amit Antarkar, Hyderabad (IN); Abhijit Deshmukh, Hyderabad (IN); Jeffrey P. Smith, Morgantown, WV (US)

(73) Assignee: Mylan Laboratories Limited (IN)

(*) Notice: Subject to any disclaimer, the term of this patent is extended or adjusted under 35 U.S.C. 154(b) by 445 days.

(21) Appl. No.: 18/251,923

(22) PCT Filed: Nov. 3, 2021

(86) PCT No.: PCT/IB2021/060148
§ 371 (c)(1),
(2) Date: May 5, 2023

(87) PCT Pub. No.: WO2022/097024
PCT Pub. Date: May 12, 2022

(65) Prior Publication Data

US 2024/0277726 A1 Aug. 22, 2024

(30) Foreign Application Priority Data

Nov. 6, 2020 (IN) ............................ 202041048559

(51) Int. Cl.
*A61K 31/5415* (2006.01)
*A61K 9/20* (2006.01)
*A61K 9/50* (2006.01)

(52) U.S. Cl.
CPC ........ *A61K 31/5415* (2013.01); *A61K 9/2009* (2013.01); *A61K 9/2027* (2013.01); *A61K 9/2054* (2013.01); *A61K 9/2081* (2013.01); *A61K 9/5078* (2013.01)

(58) Field of Classification Search
CPC .............. A61K 31/5415; A61K 9/2009; A61K 9/2027; A61K 9/2054; A61K 9/2081; A61K 9/5078
See application file for complete search history.

(56) References Cited

U.S. PATENT DOCUMENTS

| | | | |
|---|---|---|---|
| 9,526,734 | B2 | 12/2016 | Bosch |
| 9,649,318 | B2 | 5/2017 | Bosch |
| 9,808,468 | B2 | 11/2017 | Bosch |
| 9,821,075 | B2 | 11/2017 | Tabuteau |
| 10,265,399 | B2 | 4/2019 | Tabuteau |
| 10,265,400 | B2 | 4/2019 | Tabuteau |
| 10,307,484 | B2 | 6/2019 | Tabuteau |
| 10,369,224 | B2 | 8/2019 | Tabuteau |
| 10,369,225 | B2 | 8/2019 | Tabuteau |
| 10,426,839 | B2 | 10/2019 | Tabuteau |
| 10,463,736 | B2 | 11/2019 | Tabuteau |
| 10,709,713 | B2 | 7/2020 | Cooper |
| 2005/0053669 | A1 | 3/2005 | Friedl et al. |
| 2007/0077296 | A1 | 4/2007 | Folger et al. |
| 2011/0160273 | A1 | 6/2011 | Buschmann et al. |
| 2012/0149692 | A1 | 6/2012 | Hanna et al. |
| 2013/0224151 | A1 | 8/2013 | Pearson et al. |
| 2017/0281640 | A1 | 10/2017 | Romero Medina et al. |
| 2020/0085835 | A1 | 3/2020 | Bosch |
| 2022/0184095 | A1 | 6/2022 | Allan et al. |
| 2023/0172943 | A1 | 6/2023 | Allan et al. |
| 2024/0277726 | A1 | 8/2024 | Patil et al. |
| 2025/0352478 | A1 | 11/2025 | Patil et al. |
| 2025/0352479 | A1 | 11/2025 | Patil et al. |
| 2025/0352552 | A1 | 11/2025 | Patil et al. |

FOREIGN PATENT DOCUMENTS

| | | | |
|---|---|---|---|
| CA | 2976272 | C | 9/2018 |
| CN | 1233323 | A | 12/2005 |
| CN | 107405359 | A | 11/2017 |
| CN | 107970219 | A | 5/2018 |
| EP | 4008319 | B1 | 6/2022 |
| JP | 2007197357 | A | 8/2007 |
| JP | 2011207875 | A | 10/2011 |
| JP | 4965130 | B2 | 7/2012 |
| NZ | 540226 | A | 3/2008 |
| WO | 2007011349 | A1 | 1/2007 |
| WO | 2009094155 | A1 | 7/2009 |
| WO | 2011086194 | A1 | 7/2011 |
| WO | 2015191595 | A1 | 12/2015 |
| WO | 2020219406 | A1 | 10/2020 |

(Continued)

OTHER PUBLICATIONS

Strickley et al. Formulation Challenges of Prodrugs. Prodrugs. 2007. Chapter 4.1.2. 383-410 (Year: 2007).*
H. Suzuki et al., "Amorphous Solid Dispersion of Meloxicam Enhanced Oral Absorption in Rats With Impaired Gastric Motility", Journal of Pharmaceutical Sciences 2018; 107: 446-452 (Year: 2018).
Strickley, R., et al., "Formulation Challenges of Prodrugs", Prodrugs, 2007, Chapter 4.1.2, pp. 383-410.
Rechberger, T., et al., "Analgesic Efficacy and Safety of Intravenous Meloxicam in Subjects With Moderate-to-Severe Pain After Open Abdominal Hysterectomy: A Phase 2 Randomized Clinical Trial", Anesthesia & Analgesia, 2019, 128(6), 1309-1318.
US Food and Drug Administration MOBIC® label, Jun. 30, 2016.
Patent Cooperation Treaty (PCT), International Preliminary Report on Patentability for PCT/IB2021/060148, 7 pages, with a mailing date of May 8, 2023.

(Continued)

*Primary Examiner* — Clinton A Brooks
*Assistant Examiner* — Jerica Katlynn Wilson

(57) ABSTRACT

The present invention relates to novel pharmaceutical composition comprising meloxicam for the treatment of acute pain, wherein the composition comprises at least a hydrophilic polymer and one or more alkalizing agents or combinations thereof.

22 Claims, No Drawings

(56) References Cited

FOREIGN PATENT DOCUMENTS

| | | | |
|---|---|---|---|
| WO | 2020262618 | A1 | 12/2020 |
| WO | 2021216545 | A1 | 10/2021 |
| WO | 2022097024 | A1 | 5/2022 |

OTHER PUBLICATIONS

Co-pending U.S. Appl. No. 19/285,358, filed Jul. 30, 2025, published as U.S. Appl. No. 19/285,358, filed Jul. 30, 2025 (noted above).
Co-pending U.S. Appl. No. 19/285,330, filed Jul. 30, 2025, published as U.S. Appl. No. 19/285,330, filed Jul. 30, 2025 (noted above).
Co-pending U.S. Appl. No. 17/920,233, filed Oct. 20, 2022, published as U.S. Appl. No. 17/920,233, filed Oct. 20, 2022 (noted above).
Co-pending U.S. Appl. No. 19/285,261, filed Jul. 30, 2025, published as U.S. Appl. No. 19/285,261, filed Jul. 30, 2025 (noted above).
Co-pending U.S. Appl. No. 19/397,231, filed Nov. 21, 2025.
Co-pending U.S. Appl. No. 19/397,427, filed Nov. 21, 2025.
Co-pending U.S. Appl. No. 19/397,383, filed Nov. 21, 2025.
Co-pending U.S. Appl. No. 19/397,290, filed Nov. 21, 2025.
Robarge, JD., et al.,. "Rat as a Predictive Model for Human Clearance and Bioavailability of Monoclonal Antibodies". Antibodies (Basel). Dec. 24, 2024;14(1):2.
Pollak, RA., et al., "Efficacy and Safety of Intravenous Meloxicam in Patients With Moderate-to-Severe Pain Following Bunionectomy: A Randomized, Double-Blind, Placebo-controlled Trial". The Clinical Journal of Pain. Oct. 2018, 34(10):p. 918-926.
Pi, J., et al., "A Nano-Cocrystal Strategy to Improve the Dissolution Rate and Oral Bioavailability of Baicalein". Asian Journal of Pharmaceutical Sciences, Mar. 2019, vol. 14, No. 2, pp. 154-164.
Nair, AB., et al., "A Simple Practice Guide For Dose Conversion Between Animals and Human". J Basic Clin Phar., Mar. 2016. 7(2):27-31.
Lillethorup, IA., et al., "Prodrugs and Their Activation Mechanisms for Brain Drug Delivery". RSC Med Chem. 2025; 16:1037.
Sirisha, V., et al., "A Review of Pellets and Pelletization Process—A Multiparticulate Drug Delivery System" IJPSR, 2013;4(6)2145-2158.
Brady, J. et al., "Developing Solid Oral Dosage Forms". Chap 7 Polymer Properties and Characterization. 2017: 181-223.
Notice of Reasons for Refusal for JP Patent Application No. 2023-528011, with a mailing date of Oct. 31, 2025.
Karolewicz, et al., " A Review of Polymer as Multifunctional Excipients in Drug Dosage Form Technology" Saudi Pharmaceutical Journal. Mar. 7, 2015; 24(5):525-536.
Edited by Japan Pharmaceutical Excipients Association, COPOLYVIDON, Japanese Pharmaceutical Excipients Directory, first printing, 2016, pp. 203-204.
VivlodexTM (meloxicam) capsules, for oral use. Label approved by U.S. Food and Drug Administration in Oct. 2015.
AnjesoTM Package Insert, U.S. Food and Drug Administration, Revised Apr. 2021.
Auvinet et al., "Comparison of the Onset and Intensity of Action of Intramuscular Meloxicam and Oral Meloxicam in Patients in Acute Sciatica", Clinical Therapeutics, 17(6):1078-90, (1995).
Combe et al., "Comparison of Intramuscular and Oral Meloxicam in Rheumatoid Arthritis Patients", Inflammatory Research, 50(1):10-16, (2001).
Elfadadny et al., "A Comparative Time-dependent Study of Hematology, serum Gastrin Concentrations, and Gastroscopic Assessment of Meloxicam-induced Gastric Ulceration in Dogs", Journal Vet Internal Medicine. Sep. 35(5):2196-2204, (2021).
Engelhardt et al., "Anti-inflammatory, Analgesic, Antipyretic and Related Properties of Meloxicam, a New Non-steroidal Anti-inflammatory Agent with Favourable Gastrointestinal Tolerance", Inflamm Res, 44: 423-433,(1995).
Engelhardt et al., "Pharmacology of Meloxicam, A New Non-steroidal Anti-inflammatory Drug with An Improved Safety Profile Through Preferential Inhibition of COX-2", British Journal Rheumatology, 35:4-12, (1996).
Gottlieb et al., "Evaluation of the Safety and Efficacy of an Intravenous Nanocrystal Formulation of Meloxicam in the Management of Moderate-to-severe Pain after Bunionectomy" Journal of Pain Research, 16(11): p. 383-393, (2018).
Isiordia-Espinoza et al., "Pre-emptive Analgesic Effectiveness of Meloxicam Versus Tramadol After Mandibular Third Molar Surgery: A Pilot Study", J Oral Maxil Surg, 50 (1):31-36, (2012).
MOBIC Clinical SBOA (1999). Summary basis of approval of Mobic (Meloxicam). Clinical USFDA. Boehringer Ingelheim Pharmaceuticals Inc. Dec. 16, 1999.
MOBIC Label (2024). Approved product labeling for MOBIC® (meloxicam) tablets, for oral use. USFDA. Boehringer Ingelheim Pharmaceuticals Inc.
MOBIC Nonclinical SBOA (1999). Summary basis of approval of MOBIC (MELOXICAM) nonclinical. USFDA. Boehringer Ingelheim Pharmaceuticals Inc. Sep. 15, 1999.
Moeremans et al., "Pharmacokinetics and Absolute Oral Bioavailability of Meloxicam in Guinea Pigs (Cavia porcellus)", Vet Anesthesia and Analgesia 46:548-555, (2019).
Nunamaker et al., "Evaluation of Analgesic Efficacy of Meloxicam and 2 Formulations of Buprenorphine After Laparotomy in Female Sprague Dawley Rats", Journal of the American Assoc for Laboratory Animal Science, 57(5):498-507, (2018).
Tubbs et al., "Effects of Buprenorphine, Meloxicam, and Flunixin Meglumine as Postoperative Analgesia in Mice" Journal American Assoc Lab Animal Sci, 2:185-191, (2011).
Bekker A., et al., "Meloxicam in the Management of Post-operative Pain: Narrative Review". J Anaesthesiol Clin Pharmacol. Oct.-Dec. 2018;34(4):450-457.
https://www.accessdata.fda.gov/drugsatfda_docs/label/2012/020938s022lbl.pdf (accessed Jul. 21, 2025) (MOBIC® label, 2012).

* cited by examiner

PHARMACEUTICAL COMPOSITION COMPRISING MELOXICAM

CROSS REFERENCE TO RELATED APPLICATIONS

The present application is a U.S. national stage application under 35 U.S.C. § 371 of International Patent Application No. PCT/IB2021/060148, filed on Nov. 3, 2021, which claims priority to Indian Patent Application number 202041048559, filed on Nov. 6, 2020, which is hereby incorporated by reference in its entirety.

FIELD OF THE INVENTION

The present invention relates to a novel pharmaceutical composition comprising meloxicam or pharmaceutically acceptable salts, solvates, enantiomers or mixtures thereof with improved solubility, dissolution, and pharmacokinetic characteristics.

BACKGROUND OF THE INVENTION

The absorption of an orally delivered medication is a critical physiological process that transports the active pharmaceutical ingredient (API) into the bloodstream and enables the distribution, metabolism and excretion of the API in the body. Solubility and permeability are two physical properties that may affect oral drug absorption. Accordingly, the US Food and Drug Administration (FDA) classifies orally administered APIs based upon solubility and permeability in the Biopharmaceutics Classification System (BCS). Therefore, much effort has been devoted to the improvement of drug solubility in pharmaceutical development, with a special emphasis on APIs exhibiting poor dissolution profiles.

Meloxicam is a nonsteroidal anti-inflammatory drug (NSAID) that exhibits anti-inflammatory, analgesic and antipyretic activities, and is classified under BCS class II. Like other NSAIDs, the primary mechanism of action of meloxicam is via inhibition of the cyclooxygenase (COX-2) enzyme system resulting in decreased prostaglandin synthesis.

Meloxicam, an oxicam derivative, is a member of the enolic acid group of NSAIDs. It is chemically designated as 4-hydroxy-2-methyl-N-(5-methyl-2-thiazolyl)-2H-1,2-benzothiazine-3-carboxamide-1,1-dioxide and is depicted by the following chemical structure:

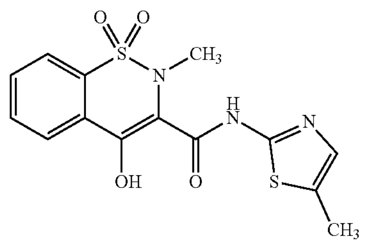 [SMILES: Cc1cnc(NC(=O)C2=C(O)c3ccccc3S(=O)(=O)N2C)s1]

Meloxicam has been developed originally by Boehringer Ingelheim and marketed in Europe as Meloxyl as an oral suspension for the treatment of rheumatoid arthritis, short term use in osteoarthritis, and ankylosing spondylitis. In the United States it is marketed as MOBIC® for the relief of the signs and symptoms of osteoarthritis. Meloxicam is manufactured either as a tablet (7.5 and 15 mg dose) or as an oral suspension (7.5 mg/5 ml dose). The form of meloxicam used in the marketed product, MOBIC®, is the pure form of meloxicam.

The absorption of meloxicam has been studied following its administration via intramuscular, oral, and rectal routes. The bioavailability of a single 30 mg oral dose of meloxicam is 89% as compared to a 30 mg intravenous bolus injection. Meloxicam capsules have been shown to be bioequivalent to MOBIC® (Meloxicam) 15 mg tablets. Following single intravenous doses, dose-proportional pharmacokinetics were shown in the range of 5 mg to 60 mg. After administration of multiple oral doses of meloxicam, the pharmacokinetics is dose-proportional in the range of 7.5 to 15 mg. The rate or extent of absorption is not affected by multiple dose administration. Mean $C_{max}$ was achieved in 4-5 hours after a 7.5 mg meloxicam tablet was taken under fasted conditions, indicating a prolonged drug absorption. A second meloxicam concentration peak occurring at approximately 12 to 14 hours post-dose, suggested gastrointestinal recirculation.

Under steady state fed conditions in healthy adult males, the 7.5 mg tablets have a mean $C_{max}$ of 1.05 μg/mL, a $T_{max}$ of 4.9 hrs, and a $t_{1/2}$ of 20.1 hours. Under steady state fed conditions in elderly males and females, the 15 mg tablets have a $C_{max}$ of 2.3 and 3.2 μg/ml respectively, a $T_{max}$ of 5 and 6 hrs respectively, and a $t_{1/2}$ of 21 and 24 hrs respectively [See *MOBIC® (meloxicam): Prescribing Information and Medication Guide; approved by U.S. FDA for osteoarthritis* Apr. 13, 2000].

Meloxicam is practically insoluble in water, with higher solubility observed in strong acids and bases. It is very slightly soluble in methanol. Meloxicam has an apparent partition coefficient (log $P)_{app}$=0.1 in n-octanol/buffer pH 7.4. Meloxicam has pKa values of 1.1 and 4.2. In particular, the solubility of meloxicam varies depending upon pH and solvent polarity due to interconversion between ionization states. Because of its low solubility under acidic conditions, orally delivered meloxicam exhibits a $T_{max}$ (time to reach maximum concentration) of 4-6 hours in humans.

Maximum plasma concentration ($C_{max}$) of meloxicam 15 mg tablets was achieved after 5-6 hours ($T_{max}$) when administered after breakfast. The onset of action of meloxicam occurs much earlier than $T_{max}$. The $C_{max}$ occurred later ($T_{max}$ was doubled) when meloxicam was administered in a fasted state [Turck D, Busch U, Heinzel G, Narjes H. Clinical pharmacokinetics of meloxicam. Eur J Rheumatol Inflamm 1995; 15:22-34]. When used chronically, NSAIDs are typically administered after a meal; thus, $C_{max}$ (5-6 hours) is the more clinically relevant figure, but it is not suitable for the treatment of acute pain.

Prior art methods of increasing the bioavailability of meloxicam include increasing its solubility by forming a cyclodextrin complex of the drug [see U.S. Pat. No. 6,284,269 (the '269 patent)] or by forming a salt of meloxicam with an inorganic or organic base (see U.S. Pat. Pub. No. US 2002/0035107 A1). Further, the '269 patent describes methods for producing pharmaceutical compositions containing meloxicam and characterized by improved wettability, solubility in water. Such compositions are prepared by modifying the crystalline structure of the drug through dry or wet mechanical homogenization with additional components that are selected from groups of oligosaccharides and alkalizing agents.

U.S. Pat. No. 9,821,075 (the '075 patent) discloses a dosage form comprising an inclusion complex of meloxicam in a cyclodextrin, and a bicarbonate, wherein the complex is formed by mixing meloxicam and the cyclodextrin in a solution and drying the solution to form the complex. Further, the pharmaceutical composition results in increased bioavailability (e.g., reduced $T_{max}$, increased $C_{max}$, increased AUC, etc.) of the meloxicam from the dosage form as compared to a dosage form containing meloxicam but not containing a cyclodextrin, an acid inhibitor, or a buffering agent (such as a bicarbonate).

Enhancement of meloxicam's low aqueous solubility has been the subject of many publications, by using different solvents (Sreedhar et al, AAPS Pharma Sci. Tech. 2003) or salt formation (Choi et al, EU J. Pharm and Biopharm. 65, 2007, 99-103) or complexing with metals (Cini et al, J. Chem. Soc. Dalton Trans, 2002,1888-1897). Preparation of different crystalline polymorphic forms of meloxicam are disclosed in the literature, see for example U.S. Pat. No. 6,967,248 and U.S. Pub. No. 2006/0025408 A1. In addition, dissolution improvements of meloxicam are also disclosed in U.S. Pat. No. 6,869,948 and WO 99/09988.

Further polyvinyl caprolactam-polyvinyl acetate-polyethylene glycol graft copolymer was used successfully with Povidone and other excipients to enhance solubility of poorly soluble drug meloxicam (Noor et al., Pak. J. Pharm. Sci., 2017, pp. 407-414).

In addition, there are several approaches currently used to formulate poorly soluble active agents. One approach is to prepare the active agent as a soluble salt, and where this approach cannot be employed, alternate (usually physical) approaches are employed to improve the solubility of the active agent. Alternate approaches generally subject the active agent to physical conditions that change the agent's physical and or chemical properties to improve its solubility. These include process technologies such as micronization, modification of crystal or polymorphic structure, development of oil-based solutions, use of co-solvents, surface stabilizers or complexing agents, micro-emulsions, supercritical fluid and production of solid dispersions or solutions. More than one of these processes may be used in combination to improve formulation of a particular therapeutic material. Many of these approaches commonly convert a drug into an amorphous state, which generally leads to a higher dissolution rate. However, formulation approaches that result in the production of amorphous material are not common in commercial formulations due to concerns relating to stability and the potential for material to re-crystallize. Generally, these approaches have involved different complex methods, different polymorphic and salt forms as well as some solid-state formulations which sometimes involve generation of certain salt forms or complexing with metal ions.

Because of these limitations related to the low aqueous solubility of meloxicam and higher $T_{max}$, there is a need to develop novel pharmaceutical composition of meloxicam that have improved solubility, dissolution, and rapid drug release with increased rate of absorption which results into lower $T_{max}$. This will be a clinical benefit in acute pain treatment.

SUMMARY AND OBJECTIVE OF THE INVENTION

One of the objectives of the present invention is to provide novel pharmaceutical composition of meloxicam for the treatment of acute pain, wherein the composition provides rapid drug release with increased rate of absorption.

Another objective of the present invention is to provide novel pharmaceutical composition comprising meloxicam for the treatment of acute pain, wherein the composition provides rapid drug release with increased rate of absorption in human subjects under fasting condition.

Yet another objective of the present invention is to provide novel pharmaceutical composition comprising meloxicam for the treatment of acute pain, wherein the composition is free of cyclodextrin and its derivatives.

Another objective of the invention is to prepare the novel pharmaceutical composition comprising meloxicam for treatment of acute pain, wherein the composition comprises meloxicam, at least a hydrophilic polymer, and one or more alkalizing agents or the combinations thereof.

Another objective of the invention is to prepare the novel pharmaceutical composition comprising meloxicam for the treatment of acute pain, wherein the composition is prepared by the method comprising the steps of embedding the Meloxicam in alkaline surroundings.

Inventors of the novel pharmaceutical composition of the present invention for the treatment of acute pain have now surprisingly found that the solubility and bioavailability of meloxicam can be improved by embedding the meloxicam in alkaline surroundings with at least a hydrophilic polymer and one or more alkalizing agents or the combinations thereof.

DETAILED DESCRIPTION OF THE EMBODIMENTS OF THE INVENTION

Described herein is a novel pharmaceutical composition of meloxicam for the treatment of acute pain, wherein the composition comprises at least a hydrophilic polymer and one or more alkalizing agents or combinations thereof. Additionally the pharmaceutical composition has improved pharmacokinetic properties such as $T_{max}$, $C_{max}$ and AUC.

Technologies for increasing drug solubility include chemical modification such as prodrug or salt formation; physical modification such as solid dispersions, nanocrystals and nanoparticles, co-crystals, and loading on porous structures; alteration of solvent composition such as pH adjustments, co-solvents & wetting agents; carrier systems such as cyclodextrins, inclusion complexes, liposomes, polymeric micelles, emulsions, microemulsions & amphiphilic polymers, surfactant dispersions, micronization by colloid mills or jet mills and likewise. Solid dispersion has often proved to be the most commonly used technique in improving dissolution of poorly soluble active pharmaceutical ingredients because it is simple, economic, and advantageous.

The term solid dispersion refers to a group of solid products containing at least two different components, generally a hydrophilic polymeric matrix and a hydrophobic drug. The matrix can be either crystalline or amorphous. The drug can be dispersed molecularly, in amorphous particles (clusters) or in crystalline particles.

The advantages of solid dispersions are increased wettability due to dispersion in a hydrophilic carrier; reduced drug particle size and hence increased surface area in two-phase solid dispersions; reduced crystallinity or creation of amorphous systems.

Various methods of forming a solid dispersion include spray drying, slow evaporation at low temperature, rotary evaporation, freeze drying, spin drying, traditional melt cool method, hot stage extrusion, melt agglomeration, solvent evaporation such as vacuum drying, hot plate drying, and super critical fluid drying.

In the present invention, the novel pharmaceutical composition of meloxicam for the treatment of acute pain comprises a solid dispersion of meloxicam with at least a hydrophilic polymer and one or more alkalizing agents, or combinations thereof. During solid dispersion, the drug converts from crystalline to amorphous form.

In one of the preferred embodiments of the present invention, the novel meloxicam pharmaceutical composition is prepared by the method comprising the steps of embedding the meloxicam in alkaline surroundings.

Meloxicam is embedded in alkaline surroundings in order to keep the pH of microenvironment towards the alkaline side so that it ensures the dissolved drug does not precipitate immediately in the acidic dissolution media. This will ensure very rapid absorption of meloxicam in vivo and result in higher $C_{max}$ and shorted $T_{max}$ profiles as compared to the reference product MOBIC® (Meloxicam) 15 mg tablets.

In one embodiment of the present invention, the novel pharmaceutical composition comprising meloxicam for the treatment of acute pain, the composition comprises a hydrophilic polymer that is used to prepare solid dispersion of meloxicam. Useful hydrophilic polymers include, but are not limited to, copovidone, hypromellose, povidone, hydroxy propyl cellulose, hydroxy ethyl cellulose, PEG 6000, PEG 8000, PEG 20000, Lutrol F-127, or any combination thereof. Any other hydrophilic polymer known to the skilled person and found suitable for the pharmaceutical composition according to the invention may also be used in the pharmaceutical composition according to the invention.

In a further embodiment of the present invention, the novel pharmaceutical composition of meloxicam for the treatment of acute pain, release rate and absorption of meloxicam can be improved with the aid of alkalizing agents. The alkalizing agent can include, but is not limited to, ammonium hydroxide, sodium phosphate, sodium acetate, sodium carbonate, sodium bicarbonate, meglumine, ethylamine, triethylamine, ethanediamine, tromethamine, lysine, arginine, histidine, sodium hydroxide, or any combination thereof. Any other alkalizer known to the skilled person and found suitable for the pharmaceutical composition according to the invention may also be used in the pharmaceutical composition according to the invention.

In one embodiment of the present invention, the novel pharmaceutical composition comprising meloxicam for the treatment of acute pain, the composition comprises an alkalizing agent less than about 400 mg; preferably about 100-400 mg; or any amount in a range bounded by, or between, any of these values.

The novel meloxicam pharmaceutical composition of the present invention may be in the form of a tablet or capsule or any other oral dosage form comprising meloxicam, a hydrophilic polymer and one or more alkalizing agents or the combinations thereof, to reduce or eliminate pain or inflammation in a patient upon administration of one or more of said unit dosage forms. The components of the novel pharmaceutical composition may be in an immediate release dosage form.

The novel pharmaceutical composition comprising meloxicam for the treatment of acute pain can be prepared by any method known to person skilled in the art.

The novel pharmaceutical composition comprising meloxicam for the treatment of acute pain is preferably an oral pharmaceutical composition according to the invention, further comprising one or several pharmaceutically acceptable excipients.

The novel pharmaceutical composition comprising meloxicam for the treatment of acute pain is a composition comprising meloxicam and at least one pharmaceutical acceptable excipient, wherein the composition is free of cyclodextrin and its derivatives.

Excipients to be used in the compositions of the present invention are preferably selected from the group consisting of diluents, binders, hydrophilic polymers, lubricants, glidants, disintegrants, alkalizing agents, coating materials and solvents. Any other excipient known to the skilled person and found suitable for the composition according to the invention may also be used in the composition according to the invention.

The novel meloxicam pharmaceutical composition of the present invention may comprise one or more suitable inert pharmaceutical diluents selected from the group consisting of sucrose, dextrose, lactose, mannitol, microcrystalline cellulose, fructose, xylitol, sorbitol, starches, and the like, and mixtures thereof.

One or several binders according to the invention are preferably selected from the group consisting of polyvidone (used synonymously for povidone), methylcellulose, hydroxypropylmethylcellulose(HPMC)/hypromellose, starch, gelatin, and hydroxy methylcellulose. Any other binder known to the skilled person and found suitable for the composition according to the invention may also be used in the composition according to the invention.

The novel meloxicam pharmaceutical composition of the present invention may also comprise one or more disintegrants selected from the group consisting of croscarmellose sodium, sodium starch glycolate, pregelatinised starch and cross-linked polyvinylpyrrolidone. Any other disintegrant known to the skilled person and found suitable for the composition according to the invention may also be used in the composition according to the invention.

The novel meloxicam pharmaceutical composition of the present invention may also comprise one or more lubricants selected from the group consisting of magnesium stearate, calcium stearate, glyceryl behenate, polyethylene glycol, stearic acid, and talc. Any other lubricant known to the skilled person and found suitable for the composition according to the invention may also be used in the composition according to the invention.

The novel meloxicam pharmaceutical composition according to the present invention may also comprise one or more glidants include, but are not limited to, calcium phosphate, calcium silicate, powdered cellulose, magnesium trisilicate, silicon dioxide, talc, colloidal silica, colloidal silica anhydrous and the like.

The novel meloxicam pharmaceutical composition according to the present invention may also comprise one or more solvents that include, but are not limited to, isopropyl alcohol, methanol, ethanol, dichloro methane, acetone and the like. Other Suitable solvents can also be selected from dimethylacetamide (DMA), dimethyl sulfoxide (DMSO), 1-methyl-2-pyrrolidone (NMP), 1,3-dimethyl-2-imidazolidinone (DMI), acetone, tetrahydrofuran (THF), dimethylformamide (DMF), propylene carbonate (PC), glycerine, dimethyl isosorbide and mixtures thereof. Aqueous solvent includes water. Combination of aqueous and non-aqueous solvents can also be used.

The novel meloxicam pharmaceutical composition according to the present invention may also comprise one or more coating materials that include, but are not limited to, film-forming substances, e.g. hydroxypropyl methyl cellulose (hypromellose), hydroxyl propyl cellulose, methyl cellulose, polyvinyl alcohol. Optionally, other auxiliary substances, such as plasticizers, and colorants, may be present. Preferred plasticizers are polyethylene glycol (Macrogols e.g. Macrogol 6000), triethyl citrate and triacetin. The film coating may also contain excipients such as, excipients for better film adhesion, preferably lactose and/or stearic acid, release agents/antiadhesive agents, preferably talcum and/or glycerol monostearate, and colorants (pigments and lakes). A preferred blend of hydroxypropyl methylcellulose, a plasticizer and a colorant is commercially available under the tradename Opadry®.

The present invention of a novel pharmaceutical composition comprising meloxicam for the treatment of acute pain preferably also relates to a novel pharmaceutical composition comprising 0.5 to 100 mg of meloxicam. The more preferred compositions contain 1 to 50 mg of meloxicam, or 5 to 50 mg of meloxicam. The even more preferred compositions contain 1 to 20 mg of meloxicam, or 1.25 to 15 mg meloxicam, or 7.5 to 15 mg of meloxicam. Most preferred composition contains 1 mg, 1.25 mg, 2.5 mg, 5 mg, 7.5 mg, 10 mg, 12.5 mg or 15 mg of meloxicam.

In some embodiments of the present invention, the novel meloxicam pharmaceutical composition may be administered to relieve arthritis pain. In some embodiments, the pharmaceutical composition may be administered to relieve other signs and/or symptoms of arthritis. Examples of arthritis include, but are not limited to pain associated with osteoarthritis, rheumatoid arthritis, juvenile rheumatoid arthritis, erosive osteoarthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome. In other embodiments, the arthritis pain may be chronic or acute. In some embodiments the pharmaceutical composition may be administered to relief the signs and/or symptoms of an arthritis including but not limited to osteoarthritis.

In some embodiments the present invention, the novel meloxicam pharmaceutical composition may be used for treating or alleviating of inflammatory disease, pain from or symptoms of an inflammatory disease, toothache, ache after tooth extraction, sore throat, otalgia, arthralgia, lumbago, myalgia, headache, muscle stiffness of shoulder, pain from a pulled muscle or sprain, pain from tense muscles, pain from swelling, pain of contusion, pain of fracture, pain of sprain or bruising, pain from burns, menstrual pain (dysmenorrhea), traumatic pain, chill, exothermic reaction, and/or cold and various symptoms of cold such as sore throat, chill, pyrexia or fever, arthralgia, and muscle pain.

The term "Acute pain" refers to sudden pain from a specific cause (injury, infection, inflammation, etc.) that has lasted for a limited period of time (as opposed to chronic pain). "Chronic pain" refers to a persistent state of pain. Chronic pain is often associated with long-term incurable or intractable medical conditions or diseases. "Procedural pain" refers to pain arising from a medical, dental surgical or other procedure wherein the procedure may be planned or associated with acute trauma.

The term "pain" as used herein to all types of pain, in particular moderate to severe pain. Pain includes neuropathic pain, post-operative pain, chronic lower back pain, cluster headaches, herpes neuralgia, phantom limb pain, central pain, dental pain, visceral pain, surgical pain, bone injury pain, pain during labor and delivery, pain resulting from burns, postpartum pain, migraine, angina pain, genitourinary tract-related pain, including cystitis and nociceptive pain. In some instances, the pain is acute pain. The term post-operative pain, or post-surgical pain, as used herein refers to a subject's pain after surgery. In some aspects, provided herein are methods for treating pain in a human subject, comprising administering to a human subject in need thereof a pharmaceutical composition that comprises meloxicam, wherein the human subject experiences increased pain relief compared to a human subject administered with a marketed formulation.

Measures of bioavailability are well known in the art and include the area under the plasma concentration-time curve (AUC), the maximum concentration ($C_{max}$), and the time to reach $C_{max}$ ($T_{max}$).

AUC is a measurement of the area under the plasma concentration-time curve and is representative of the amount of drug absorbed following administration of a single dose of a drug (Remington: The Science and Practice of Pharmacy, (Alfonso R. Gennaro ed. 2000), page 999).

$C_{max}$ is the maximum plasma concentration achieved after oral drug administration (Remington, page 999).

$T_{max}$ is the amount of time necessary to achieve the $C_{max}$ after oral drug administration and is related to the rate of absorption of a drug (Remington, page 999).

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within one (1) or more than one (1) standard deviations, per the practice in the art. Alternatively, "about" can mean a range of up to 20%, preferably up to 10% of a given value.

EXAMPLE I

TABLE 1

Composition of Meloxicam tablets 15 mg

| Ingredients | Ex. 1 mg/tab | Ex. 2 mg/tab | Ex. 3 mg/tab | Ex. 4 mg/tab | Ex. 5 mg/tab | Ex. 6 mg/tab | Ex. 7 mg/tab |
|---|---|---|---|---|---|---|---|
| Alkalizer solution 1 | | | | | | | |
| 1 Sodium bicarbonate (Part 1) | 50.000 | 50.000 | 50.000 | 50.000 | 50.000 | 50.000 | 10.000 |
| 2 Hypromellose E3LV (Part 1) | 5.000 | 5.000 | 5.000 | 5.000 | 5.000 | 5.000 | 1.000 |
| 3 Purified water | q.s | q.s | q.s | q.s | q.s | q.s | q.s |
| Dry mix | | | | | | | |
| 4 Microcrystalline cellulose PH101 | 270.00 | 220.000 | 220.000 | 220.000 | 220.00 | 220.000 | 220.000 |
| 5 Crospovidone (Polyplasdone XL 10) | 30.000 | 30.000 | 30.000 | 30.000 | 30.000 | 30.000 | 30.000 |
| 6 Colloidal Silicon dioxide (Aerosil 200) | 25.000 | 15.000 | 15.000 | 15.000 | 15.000 | 15.000 | 15.000 |
| 7 Sodium bicarbonate (Part 2) | 130.000 | 70.000 | 70.000 | 70.000 | 70.000 | 70.000 | 10.000 |
| Drug-Binder solution | | | | | | | |
| 8 Meloxicam API | 15.000 | 15.000 | 15.000 | 15.000 | 15.000 | 15.000 | 15.000 |
| 9 Sodium bicarbonate (Part 3) | 60.000 | 60.000 | 60.000 | 60.000 | 60.000 | 60.000 | 60.000 |

TABLE 1-continued

| Composition of Meloxicam tablets 15 mg | | | | | | | |
|---|---|---|---|---|---|---|---|
| Ingredients | Ex. 1 mg/tab | Ex. 2 mg/tab | Ex. 3 mg/tab | Ex. 4 mg/tab | Ex. 5 mg/tab | Ex. 6 mg/tab | Ex. 7 mg/tab |
| 10 Copovidone (Plasdone S 630) | 105.000 | 95.000 | 95.000 | 95.000 | 95.000 | 95.000 | 95.000 |
| 11 Purified water | q.s | q.s | q.s | q.s | q.s | q.s | q.s |
| 12 Isopropyl alcohol | q.s | q.s | q.s | q.s | q.s | q.s | q.s |
| Alkalizer solution 2 | | | | | | | |
| 13 Sodium bicarbonate (Part 4) | 150.000 | 150.000 | 150.000 | 120.000 | 30.000 | 120.000 | 20.000 |
| 14 Hypromellose E3LV (Part 2) | 15.000 | 15.000 | 15.000 | 12.000 | 3.000 | 12.000 | 2.000 |
| 15 Purified water | q.s | q.s | q.s | q.s | q.s | q.s | q.s |
| Extragranular | | | | | | | |
| 16 Crospovidone (Polyplasdone XL) | 110.000 | 205.00 | 107.000 | 100.000 | 109.000 | 100.000 | 104.000 |
| 17 Sodium carbonate | — | 50.00 | — | — | — | — | — |
| 18 Colloidal silicon dioxide (Syloid 244FP) | 50.000 | 40.00 | 10.000 | 10.000 | 10.000 | 10.000 | 10.000 |
| 20 Meglumine | — | — | — | — | — | — | 50.00 |
| 21 Magnesium stearate | 10.000 | 10.00 | 8.000 | 8.000 | 8.000 | 8.000 | 8.000 |
| Core Tablet Weight | 1025.00 | 1030.00 | 850.000 | 810.000 | 720.00 | 810.00 | 650.000 |
| 22 opadry yellow 03F82657 | 30.750 | — | — | 20.250 | — | — | — |
| 23 Isopropyl alcohol | q.s | — | — | q.s | — | — | — |
| 24 P. water | q.s | — | — | q.s | — | — | — |
| Coated tablet weight | 1055.75 | — | — | 830.25 | — | — | — |

*Varying concentration of alkalizing agents such as Sodium bicarbonate, Sodium carbonate and meglumine, were evaluated.

**Total sodium bicarbonate quantity per tablet was varied from 100 mg to 400 mg and observed dissolution was found to be very rapid.

Brief Manufacturing Process:

1. Alkalizer-1 solution was prepared by dissolving Sodium bicarbonate (part 1) and hypromellose E3LV (part 1) in purified water.
2. Microcrystalline cellulose PH101, Crospovidone, colloidal silicon dioxide and sodium carbonate were sifted together and granulated with alkalizer-1 solution in first step to obtain alkalizer based granules.
3. Sodium carbonate (part 3) and Copovidone was dissolved in purified water and Meloxicam was added to this solution to form dispersion. Isopropyl alcohol is added in the dispersion with stirring to obtained meloxicam solution.
4. Alkalized granules were further granulated using meloxicam suspension of third step in fluid bed processer.
5. Alkalizer solution-2 was prepared by dissolving the Sodium bicarbonate (part 4) and hypromellose E3LV (part 2) in purified water.
6. The drug granules were further granulated using alkalizer-2 solution of fifth step to obtain drug granules.

The Extragranular

7. Crospovidone (Polyplasdone XL) and Colloidal silicon dioxide (Syloid 244FP) were sifted through suitable mesh and blended with drug granules in blender. The blend is lubricated with magnesium stearate in blender.
8. The lubricated blend was compressed using suitable tooling on rotary compression machine. The core tablets were finally coated using hydro-alcoholic dispersion of opadry in automated coating pan.

EXAMPLE II

TABLE 2

| Composition of Meloxicam tablets 15 mg - MUPS formulation | |
|---|---|
| Ingredients | Ex. 7 mg/tab |
| Alkalizer solution 1 | |
| 1 Sugar Sphere (60/80) | 100.00 |
| 2 Hypromellose E5LV (Part 1) | 20.00 |
| 3 Sodium Bicarbonate (Part 1) | 100.00 |
| 4 Purified water | q.s. |
| Drug-Binder solution | |
| 5 Meloxicam API | 15.000 |
| 6 Sodium bicarbonate (Part 2) | 60.000 |
| 7 Copovidone (Plasdone S 630) | 95.000 |
| 8 Purified water | q.s |
| 9 Isopropyl alcohol | q.s |
| Alkalizer solution 2 | |
| 10 Sodium Bicarbonate (Part 3) | 170.000 |
| 11 Hypromellose E5LV (Part 2) | 40.000 |
| 12 Purified water | q.s |
| Extragranular | |
| 13 Crospovidone (Polyplasdone XL) | 20.000 |
| 14 Microcrystalline Cellulose PH 102 (Avicel PH 102) | 365.000 |
| 15 Magnesium stearate | 10.000 |
| Core Tablet Weight | 995.00 |
| 16 Opadry White 03F58750 | 25.000 |
| 17 P. water | q.s |
| Coated tablet weight | 1020.00 |

*Alkalizing agent and drug binder solution sprayed on sugar beads. Order of addition of alkalizing agent, drug binder solution and again alkalizing agent was kept same.

Brief Manufacturing Process

1. Alkalizer 1 solution is prepared by dissolving Sodium bicarbonate (part 1) and hypromellose E5LV (part 1) in purified water.
2. Sugar sphere (60/80) was coated with Alkalizer solution-1 of first step to obtained alkalized sugar sphere.
3. Sodium carbonate (part 2) and Copovidone was dissolved in purified water and Meloxicam was added to this solution to form dispersion. Isopropyl alcohol is added in the dispersion with stirring to obtained meloxicam solution.
4. Alkalized sugar sphere were further coated using meloxicam solution of third step in fluid bed processer.
5. Alkalizer solution 2 was prepared by dissolving the Sodium bicarbonate (part 3) and hypromellose E5LV (part 2) in purified water. The drug loaded pellets were further coated using alkalizer 2 solution to obtained drug pellets.

The Extragranular

6. Crospovidone (Polyplasdone XL), Microcrystalline cellulose PH 102 (Avicel PH 102) and Colloidal silicon dioxide (Syloid 244FP) were sifted through suitable mesh and blended with drug loaded pellets in blender.
7. The blend is lubricated with magnesium stearate in blender.
8. The lubricated blend was compressed using suitable tooling on rotary compression machine.
9. The core tablets were finally coated using hydro-alcoholic dispersion of opadry in automated coating pan.

The data reported in below Table, shows rapid drug release was observed in studied dissolution condition 0.1N HCl and pH 4.5 acetate buffer. Drug release with these compositions was observed to be substantially higher than existing commercial product MOBIC® (Meloxicam) 15 mg tablets.

TABLE 3

Dissolution data for Meloxicam tablets 15 mg

Dissolution condition: 0.1N HCL, 900 ml, USP Apparatus II (Paddle), 75 rpm

| Time (minutes) | Reference product - MOBIC ® tablets 15 mg | Batch No. & % Drug dissolved Ex. 1 | Ex. 2 | Ex. 3 | Ex. 4 | Ex. 5 | Ex. 6 | Ex. 7 |
|---|---|---|---|---|---|---|---|---|
| 5 | 1 | 88 | 73 | 92 | 92 | 80 | 82 | 48 |
| 15 | 3 | 88 | 84 | 93 | 93 | 91 | 90 | 65 |
| 30 | 5 | 88 | 87 | 96 | 93 | 75 | 78 | 69 |
| 60 | 6 | 86 | 83 | 94 | 92 | 72 | 60 | 69 |

* The dissolution data for the examples 1-7 with varying concentration of alkalizing agent is presented in the table.

TABLE 4

Dissolution data for Meloxicam tablets 15 mg
Dissolution condition pH 4.5 acetate buffer, 900 ml,
USP Apparatus II (Paddle), 75 rpm

| Time (minutes) | Batch No. & % Drug dissolved Reference product - MOBIC ® tablets 15 mg | Ex. 1 | Ex. 2 | Ex. 4 | Ex. 7 |
|---|---|---|---|---|---|
| 5 | 4 | 94 | 94 | 78 | 79 |
| 15 | 7 | 96 | 98 | 96 | 81 |
| 30 | 9 | 95 | 98 | 100 | 87 |
| 60 | 11 | 95 | 98 | 98 | 89 |

The above dissolution data indicates that the tablets prepared using the mentioned invention has faster dissolution rate when compared with that of commercial reference product MOBIC® (Meloxicam) 15 mg tablets.

Pharmacokinetic Properties of Meloxicam Compositions

The pharmacokinetic profiles of the meloxicam compositions of the present invention are not substantially affected by the fasted state of the human subject ingesting the meloxicam compositions. Further, the compositions of the present invention substantially lowers the $T_{max}$ and increases the $C_{max}$ of the meloxicam composition when compared to reference product MOBIC® (Meloxicam) 15 mg tablets. Thus, it will be beneficial to treat the acute pain condition.

Preferably, the $T_{max}$ of an administered dose of a meloxicam composition of the invention is less than that of reference product MOBIC® (Meloxicam), administered at the same dosage. A preferred meloxicam composition of the invention exhibits in comparative pharmacokinetic testing with a reference product MOBIC® (Meloxicam) 15 mg tablets, in oral suspension, capsule or tablet form, a $T_{max}$ which is less than about 100%, less than about 90%, less than about 80%, less than about 70%, less than about 60%, less than about 50%, less than about 40%, less than about 30%, less than about 25%, less than about 20%, less than about 15%, or less than about 10% of the $T_{max}$ exhibited by the reference product MOBIC® (Meloxicam) 15 mg tablets.

Fast Onset of Activity

The meloxicam compositions of the present invention exhibit faster therapeutic effects. In one example, following administration of the meloxicam compositions of the present invention comprising meloxicam have a $T_{max}$ of than about 4 hours, less than about 3.5 hours, less than about 3 hours, less than about 2.75 hours, less than about 2.5 hours, less than about 2.25 hours, less than about 2 hours, less than about 1.75 hours, less than about 1.5 hours, less than about 1.25 hours, less than about 1.0 hours, less than about 50 minutes, less than about 40 minutes, less than about 30 minutes, less than about 25 minutes, less than about 20 minutes, and less than about 15 minutes of the $T_{max}$ exhibited by the reference product MOBIC® (Meloxicam) 15 mg tablets.

Increased Bioavailability

The meloxicam compositions of the present invention exhibit increased bioavailability (AUC) when compared to MOBIC® (Meloxicam) 15 mg tablets, administered at the same dose. The difference in absorption of the meloxicam composition of the present invention, when administered in the fasted state, is more than about 5%, more than about 10%, more than about 20%, more than about 30%, more than about 40%, more than about 50%, more than about 60%, more than about 70%, more than about 80%, more than about 90%, or more than about 100% of AUC exhibited by the MOBIC® (Meloxicam) 15 mg Tablets. This is an especially important feature in treating patients with acute pain while with difficulty in maintaining a fasted state.

In addition, the $C_{max}$ of a meloxicam composition of the present invention is greater than the $C_{max}$ of a reference product MOBIC® (Meloxicam) 15 mg tablets, administered at the same dosage. A preferred meloxicam composition of the invention exhibits a $C_{max}$ which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% of the $C_{max}$ exhibited by the reference product MOBIC® (Meloxicam) 15 mg tablets.

In one embodiment, following administration of the novel pharmaceutical composition comprising meloxicam for the treatment of acute pain, $C_{max}$ of the meloxicam between about 2000 ng/ml to about 3500 ng/ml; preferably between about 2200 ng/ml to about 3400 ng/ml; or any $C_{max}$ in a range bounded by, or between, any of these values.

A single-dose, randomized, two-period, two treatment, two sequence, crossover bioequivalence study was performed for test product Meloxicam Tablets 15 mg (Ex. 4) according to present invention, to reference product MOBIC® (Meloxicam) tablets 15 mg distributed by Boehringer Ingelheim Pharmaceuticals, Inc., following a single, oral dose of 15 mg administered under fasting conditions Single-dose pharmacokinetics were characterized in 18 healthy adult human subjects (two subjects were withdrawn) following administration of a single, oral 15 mg dose of study medication under fasting conditions. For the determination of the pharmacokinetic disposition of the formulations, there will be a total of 50 blood samples involving a total of 200 mL of blood collected for pharmacokinetic analysis from each subject provided they complete all blood collections in the study. There will be at least 12 days between dosing times for the treatment periods.

The bioequivalence of test product Meloxicam tablets 15 mg according to present invention, with reference product MOBIC® (Meloxicam) 15 mg tablets was assessed by a statistical comparison of various pharmacokinetic parameters derived from the plasma concentration and presented below.

TABLE 5

Summary of Pharmacokinetic Data for Meloxicam (n = 16)
Dose: 1 × 15 mg

| | Test Product (A): Meloxicam Tablets USP 15 mg | | Reference Product (B): MOBIC ® (Meloxicam) Tablets 15 mg | |
|---|---|---|---|---|
| Parameter | N | Arithmetic mean ± Std Deviation (Coeff of Variation (%)) | N | Arithmetic mean ± Std Deviation (Coeff of Variation (%)) |
| $T_{max}$ (hr)^ | 16 | 0.750 (0.333-3.500) | 16 | 4.000 (2.000-8.000) |
| T1090 (hr)^ | 16 | 0.333 (0.333-0.500) | 16 | 3.000 (1.250-6.000) |
| $C_{max}$ (ng/mL) | 16 | 2786.072 ± 558.429 (20.044) | 16 | 1611.147 ± 248.539 (15.426) |
| AUCt (ng/mL)*(hr) | 16 | 49700.363 ± 16123.474 (32.441) | 16 | 42834.546 ± 11236.963 (26.233) |
| AUCi (ng/mL)*(hr) | 16 | 55910.213 ± 24751.922(44.271) | 16 | 48233.472 ± 17534.480 (36.353 |

T1090 = Time at which concentration first exceeds 1090 ng/mL
^T1090 and $T_{max}$ are presented as Median (Range)

TABLE 6

Test (A) & Reference (B), 90% Confidence Intervals and Ratio for Meloxicam (n = 16)

| Pharmacokinetic Parameters | 90% Confidential Interval | Ratio (%) |
|---|---|---|
| $C_{max}$ (ng/ml) | (159.92%-184.44%) | 171.74% |
| $AUC_t$ (ng/ml) (hr) | (109.37%-119.24%) | 114.20% |
| $AUC_i$ (ng/mL) (hr) | (108.02%-119.00%) | 113.38% |

Based on the results provided in above tables 5 & 6, The median $T_{max}$ for meloxicam, was 5 times faster for the test product Meloxicam Tablets 15 mg, as compared to reference product MOBIC® (Meloxicam) 15 mg Tablets, (0.75 hour versus 4 hours respectively), distributed by Boehringer Ingelheim Pharmaceuticals, Inc. As expected for this formulation of meloxicam which was designed to be used for the treatment of acute pain, the test product demonstrated a more rapid absorption than MOBIC®, as evidenced by a higher $C_{max}$, higher pAUCs, shorter $T_{max}$ and a more rapid time to achieve 1090 ng/ml (set by FDA, guidance for industry, bioavailability, and bioequivalence studies for orally administered drug products—general considerations, center for drug evaluation and research [CDER], March 2003).

The invention claimed is:

1. A solid oral pharmaceutical tablet for the treatment of acute pain, the tablet comprising amorphous meloxicam and at least one pharmaceutically acceptable excipient, wherein the amorphous meloxicam is embedded in alkaline surroundings comprising one or more water-soluble alkalizing agents, and wherein the tablet provides a Tmax of meloxicam that is less than about 3 hrs in a human subject under fasting conditions.

2. The solid oral pharmaceutical tablet according to claim 1, wherein the tablet has rapid drug release with an increased rate of absorption, and wherein the tablet is free of cyclodextrin and its derivatives.

3. The solid oral pharmaceutical tablet according to claim 2, wherein the tablet has a dissolution rate of more than 90% by weight within 15 minutes.

4. The solid oral pharmaceutical tablet according to claim 1, wherein the tablet comprises about 5 mg to about 50 mg of meloxicam.

5. The solid oral pharmaceutical tablet according to claim 4, wherein the tablet comprises about 7.5 mg to about 15 mg of meloxicam.

6. The solid oral pharmaceutical tablet according to claim 1, wherein the pharmaceutically acceptable excipient comprises one or more diluents, binders, hydrophilic polymers, lubricants, glidants, disintegrants, water-soluble alkalizing agents, coating materials, solvents or combinations thereof.

7. The solid oral tablet pharmaceutical according to claim 6, comprising a hydrophilic polymer or polymers selected from the group consisting of copovidone, hypromellose, povidone, hydroxy propyl cellulose, hydroxy ethyl cellulose and combinations thereof.

8. The solid oral pharmaceutical tablet according to claim 7, wherein the hydrophilic polymer or polymers is copovidone.

9. The solid oral pharmaceutical tablet according to claim 1, comprising a water-soluble alkalizing agent or agents selected from the group consisting of sodium carbonate, sodium bicarbonate, meglumine, calcium carbonate and combinations thereof.

10. The solid oral pharmaceutical tablet according to claim 9, wherein the water-soluble alkalizing agent or agents is sodium bicarbonate.

11. The solid oral pharmaceutical tablet according to claim 10, wherein the sodium bicarbonate is present in an amount of about 100 mg to about 400 mg.

12. The solid oral pharmaceutical tablet according to claim 11, wherein the amount of sodium bicarbonate is about 300 mg.

13. The solid oral pharmaceutical tablet according to claim 1, wherein the tablet has a median Tmax of meloxicam that is less than about 90 minutes in a human subject under fasting conditions.

14. The solid oral pharmaceutical tablet according to claim 1, wherein the tablet has a median Tmax of meloxicam that is less than about 60 minutes in a human subject under fasting conditions.

15. A solid oral pharmaceutical tablet comprising amorphous meloxicam and at least one pharmaceutically acceptable excipient, wherein the amorphous meloxicam is embedded in alkaline surroundings comprising one or more water-soluble alkalizing agents, and wherein the tablet provides a plasma concentration (Cmax) of meloxicam that is between about 2000 ng/ml to about 3500 ng/ml.

16. The solid oral pharmaceutical tablet according to claim 15, wherein the Cmax of meloxicam is between about 2200 ng/ml to about 3400 ng/ml.

17. The oral tablet of claim 15, wherein the amount of meloxicam in the tablet is about 15 mg.

18. The oral tablet of claim 17, comprising a hydrophilic polymer or polymers selected from copovidone, hypromellose, povidone, hydroxy propyl cellulose, hydroxy ethyl cellulose, PEG 6000, PEG 8000, or PEG 20000, and combinations thereof.

19. The solid oral pharmaceutical tablet of claim 15, wherein the one or more pharmaceutically acceptable excipients comprise a diluent, lubricant, glidant, disintegrant, or binder, or any combination thereof.

20. The solid oral pharmaceutical tablet of claim 19, wherein the one or more pharmaceutically acceptable excipients comprise at least a lubricant.

21. The oral tablet of claim 19, wherein the excipients comprise magnesium stearate and crospovidone.

22. The solid oral pharmaceutical tablet of claim 15, wherein the water-soluble alkalizing agent is present in an amount of less than 400 mg.

* * * * *